(12) United States Patent
Hursey

(10) Patent No.: US 7,595,429 B2
(45) Date of Patent: *Sep. 29, 2009

(54) CALCIUM ZEOLITE HEMOSTATIC AGENT

(75) Inventor: Francis X. Hursey, West Hartford, CT (US)

(73) Assignee: Z-Medica Corporation, Wallingford, CT (US)

( * ) Notice: Subject to any disclaimer, the term of this patent is extended or adjusted under 35 U.S.C. 154(b) by 813 days.

This patent is subject to a terminal disclaimer.

(21) Appl. No.: 10/939,687

(22) Filed: Sep. 13, 2004

(65) Prior Publication Data

US 2005/0074505 A1    Apr. 7, 2005

Related U.S. Application Data

(60) Provisional application No. 60/502,598, filed on Sep. 12, 2003.

(51) Int. Cl.
    *A61L 15/00*    (2006.01)
(52) U.S. Cl. .................................... 604/367
(58) Field of Classification Search ................ 424/618, 424/684, 682, 27; 604/367
    See application file for complete search history.

(56) References Cited

U.S. PATENT DOCUMENTS

| | | | |
|---|---|---|---|
| 2,688,586 A | 9/1954 | Eberl et al. |
| 3,122,140 A | 2/1964 | Crowe et al. |
| 3,181,231 A | 5/1965 | Breck |
| 3,366,578 A | 1/1968 | Michalko |
| 3,538,508 A | 11/1970 | Young |
| 3,723,352 A | 3/1973 | Alexander et al. |
| 3,979,335 A | 9/1976 | Golovko et al. |
| 4,373,519 A | 2/1983 | Errede et al. |
| 4,374,044 A | 2/1983 | Schaefer et al. |
| 4,379,143 A | 4/1983 | Sherry et al. |
| 4,525,410 A | 6/1985 | Hagiwara et al. |
| 4,626,550 A | 12/1986 | Hertzenberg |
| 4,631,845 A | 12/1986 | Samuel et al. |
| 4,748,978 A | 6/1988 | Kamp |
| 4,822,349 A * | 4/1989 | Hursey et al. ............... 424/445 |
| 4,828,081 A | 5/1989 | Nordstrom et al. |
| 4,911,898 A | 3/1990 | Hagiwara et al. |
| 4,938,958 A | 7/1990 | Niira et al. |
| 4,956,350 A | 9/1990 | Mosbey |
| 5,140,949 A | 8/1992 | Chu et al. |
| 5,474,545 A | 12/1995 | Chikazawa |
| 5,486,195 A | 1/1996 | Myers et al. |
| 5,538,500 A | 7/1996 | Peterson |
| 5,556,699 A | 9/1996 | Niira et al. |
| 5,599,578 A | 2/1997 | Butland |
| 5,696,101 A | 12/1997 | Wu et al. |
| 5,716,337 A | 2/1998 | McCabe et al. |
| 5,725,551 A | 3/1998 | Myers et al. |
| 5,801,116 A | 9/1998 | Cottrell et al. |
| 5,826,543 A | 10/1998 | Raymond et al. |
| 5,941,897 A | 8/1999 | Meyers |
| 5,964,239 A | 10/1999 | Loux et al. |
| 5,981,052 A | 11/1999 | Sugiyama |
| 6,037,280 A | 3/2000 | Edwards et al. |
| 6,060,461 A | 5/2000 | Drake |
| 6,123,925 A | 9/2000 | Barry et al. |
| 6,159,232 A | 12/2000 | Nowakowski |
| 6,187,347 B1 | 2/2001 | Patterson et al. |
| 6,203,512 B1 | 3/2001 | Farris et al. |
| 6,372,333 B1 | 4/2002 | Sugiyama et al. |
| 6,428,800 B2 | 8/2002 | Greenspan et al. |
| 6,450,537 B2 | 9/2002 | Norris |
| 6,475,470 B1 | 11/2002 | Kayane et al. |
| 6,481,134 B1 | 11/2002 | Aledo |
| 6,495,367 B1 | 12/2002 | Isogawa et al. |
| 6,573,419 B2 | 6/2003 | Naimer |
| 6,630,140 B1 | 10/2003 | Grunstein |
| 6,745,720 B2 | 6/2004 | Rasner et al. |
| 6,998,510 B2 | 2/2006 | Buckman et al. |

(Continued)

FOREIGN PATENT DOCUMENTS

CA    1223208    6/1987

(Continued)

OTHER PUBLICATIONS

Hursey et al., Bandage Using Molecular Sieves, Apr. 18, 2002, International Application Published Under the PCT, WO 02/30479 A1.*

(Continued)

*Primary Examiner*—Johann R Richter
*Assistant Examiner*—Ali Soroush
(74) *Attorney, Agent, or Firm*—Knobbe, Martens, Olson & Bear LLP

(57) ABSTRACT

A composition for promoting the formation of clots in blood comprises a binder and a zeolite disposed in the binder, the zeolite having an adjusted calcium content. A method of forming a blood-clotting composition comprises the steps of providing a zeolite, combining the zeolite with a binder, and adjusting a calcium content of the zeolite to have an amount of calcium such that upon application of the composition to a wound, a heat of hydration is reduced and thereby heat transferred to the wound is reduced. A method of clotting blood flowing from a wound comprises the steps of applying a zeolite to the wound and maintaining the zeolite in contact with the wound for a predetermined amount of time. The zeolite preferably has an adjusted calcium content and is capable of producing a controllable blood clotting effect on the wound.

9 Claims, No Drawings

U.S. PATENT DOCUMENTS

| | | | |
|---|---|---|---|
| 7,371,403 | B2 | 5/2008 | McCarthy et al. |
| 2002/0197302 | A1 | 12/2002 | Cochrum et al. |
| 2003/0133990 | A1 | 7/2003 | Hursey et al. |
| 2003/0176828 | A1 | 9/2003 | Buckman et al. |
| 2003/0199922 | A1 | 10/2003 | Buckman |
| 2003/0208150 | A1 | 11/2003 | Bruder et al. |
| 2004/0005350 | A1 | 1/2004 | Looney et al. |
| 2004/0166172 | A1 | 8/2004 | Rosati et al. |
| 2004/0243043 | A1 | 12/2004 | McCarthy et al. |
| 2005/0058721 | A1* | 3/2005 | Hursey ................ 424/618 |
| 2005/0070693 | A1 | 3/2005 | Hansen et al. |
| 2005/0074505 | A1 | 4/2005 | Hursey |
| 2005/0118230 | A1 | 6/2005 | Hill et al. |
| 2005/0137512 | A1 | 6/2005 | Campbell et al. |
| 2005/0143689 | A1 | 6/2005 | Ramsey, III |
| 2006/0078628 | A1 | 4/2006 | Koman et al. |
| 2006/0116635 | A1 | 6/2006 | Van Heugten |
| 2006/0141018 | A1 | 6/2006 | Cochrum et al. |
| 2006/0172000 | A1 | 8/2006 | Cullen et al. |
| 2006/0271094 | A1 | 11/2006 | Hudson et al. |
| 2007/0031515 | A1 | 2/2007 | Stucky et al. |
| 2007/0154509 | A1 | 7/2007 | Wilcher et al. |
| 2007/0154510 | A1 | 7/2007 | Wilcher et al. |
| 2007/0154564 | A1 | 7/2007 | Stucky et al. |
| 2007/0160638 | A1 | 7/2007 | Mentkow et al. |
| 2007/0275073 | A1 | 11/2007 | Huey et al. |
| 2008/0146984 | A1 | 6/2008 | Campbell et al. |
| 2008/0199539 | A1 | 8/2008 | Baker et al. |
| 2008/0299226 | A1 | 12/2008 | Mentkow et al. |
| 2008/0319476 | A1 | 12/2008 | Ward et al. |

FOREIGN PATENT DOCUMENTS

| | | |
|---|---|---|
| EP | 0296324 | 12/1988 |
| EP | 0826822 A2 | 3/1998 |
| EP | 0888783 A1 | 7/1999 |
| EP | 1159972 | 5/2001 |
| EP | 1690553 A1 | 8/2006 |
| EP | 1714642 | 10/2006 |
| EP | 1810697 A2 | 7/2007 |
| GB | 2314842 | 1/1998 |
| JP | 61145120 | 7/1986 |
| JP | 2777279 B2 | 7/1998 |
| JP | 11-332909 A1 | 7/1999 |
| JP | 2004123651 | 7/2006 |
| WO | WO 95/05445 | 2/1995 |
| WO | WO 96/40285 | 12/1996 |
| WO | WO 99/13918 | 3/1999 |
| WO | WO 00/66086 | 11/2000 |
| WO | WO 01/82896 A1 | 8/2001 |
| WO | WO 02/30479 A1 | 4/2002 |
| WO | WO 02/060367 A1 | 8/2002 |
| WO | WO 02/074325 A1 | 9/2002 |
| WO | WO 03/074566 | 9/2003 |
| WO | WO 2005/012493 | 2/2005 |
| WO | WO 2005/027808 A1 | 3/2005 |
| WO | WO 2005/087280 | 9/2005 |
| WO | WO 2006/012218 A1 | 2/2006 |
| WO | WO 2006/088912 A2 | 8/2006 |
| WO | WO 2006/102008 | 9/2006 |
| WO | WO 2007/120342 A2 | 10/2007 |
| WO | WO 2008/036225 A2 | 3/2008 |

OTHER PUBLICATIONS

Alam et al., Comaprative Analysis of Hemostatic Agents in a Swine Model of Lethal Groin Injury, Jun. 2003, The Journal of Trauma Injury, Infection, and Critical Care, vol. 54 No. 6, pp. 1077-1082.*
M. Gielen, Solid State Organometallic Chemistry: Methods and Applications Physical Organometallic Chemistry, 1999, New York John Wiley & Sons, Ltd. (UK), V. 2, p. 156.*
Co-Pending U.S. Appl. No. 11/544,238, filed Oct. 6, 2006.
Office Action for U.S. Appl. No. 11/398,161 dated Apr. 30, 2008.
U.S. Appl. No. 11/590,427, filed Oct. 30, 2006 including prosecution history, including but not limited to Non-Final Rejection dated Aug. 19, 2008 and Final Rejection dated May 26, 2009.
U.S. Appl. No. 10/939,869, filed Sep. 13, 2004 including prosecution history, including but not limited to Non-Final Rejection dated Feb. 8, 2008, Non-Final Rejection dated Sep. 17, 2008 and Final Rejection dated Apr. 17, 2009.
U.S. Appl. No. 11/023,869, filed Dec. 27, 2004 including prosecution history, including but not limited to Requirement for Restriction/Election dated Mar. 31, 2008, Non-Final Rejection dated May 12, 2008 and Non-Final Rejection dated Dec. 11, 2008.
U.S. Appl. No. 11/054,918, filed Feb. 9, 2005 including prosecution history, including but not limited to Non-Final Office Rejection dated Mar. 18, 2008, Final Rejection dated Sep. 16, 2008 and Non-Final Rejection dated Mar. 9, 2009.
U.S. Appl. No. 11/082,716, filed Mar. 16, 2005 including prosecution history, including but not limited to Non-Final Rejection dated Oct. 9, 2008.
U.S. Appl. No. 11/303,607, filed Dec. 16, 2005 including prosecution history, including but not limited to Requirement for Restriction/Election dated Feb. 21, 2008, Non-Final Rejection dated Apr. 29, 2008 and Non-Final Rejection dated Sep. 8, 2008.
U.S. Appl. No. 11/404,126, filed Apr. 13, 2006 including prosecution history, including but not limited to Requirement for Restriction/Election dated Sep. 16, 2008 and Non-Final Rejection dated Dec. 3, 2008.
U.S. Appl. No. 11/544,238, filed Oct. 6, 2006 including prosecution history, including but not limited to Requirement for Restriction/Election dated Dec. 11, 2008; Non-Final Office Action dated May 29, 2009.
U.S. Appl. No. 11/584,079, filed Oct. 20, 2006 including prosecution history, including but not limited to Non-Final Rejection dated Apr. 6, 2009.
U.S. Appl. No. 11/592,477, filed Nov. 2, 2006 including prosecution history, including but not limited to Non-Final Rejection dated May 28, 2008 and Final Rejection dated Dec. 22, 2008.
U.S. Appl. No. 11/606,617, filed Nov. 29, 2006 including prosecution history, including but not limited to Non-Final Rejection dated Jun. 12, 2009
U.S. Appl. No. 11/633,687, filed Dec. 4, 2006 including prosecution history, including but not limited to Requirement for Restriction/Election dated Jun. 25, 2008; Non-Final Rejection dated Sep. 4, 2998 and Final Office Action dated Jun. 1, 2009.
U.S. Appl. No. 11/634,673, filed Dec. 5, 2006 including prosecution history, including but not limited to Requirement for Restriction/Election dated Apr. 9, 2008, Non-Final Rejection dated May 12, 2008, Final Rejection dated Nov. 14, 2008 and Non-Final Rejection dated May 21, 2009.
U.S. Appl. No. 11/715,057, filed Mar. 6, 2007 including prosecution history, including but not limited to Non-Final Rejection dated Aug. 20, 2008 and Final Rejection dated Apr. 2, 2009.
PCT Search Report for PCT/U52004/029809, dated Feb. 24, 2005.
PCT International Preliminary Report for PCT/US2007/016509, dated May 14, 2009.
Co-pending U.S. Appl. No. 10/939,869, filed Sep. 13, 2004.
Co-pending U.S. Appl. No. 11/023,869, filed Dec. 27, 2004.
Co-pending U.S. Appl. No. 11/054,918 filed, Feb. 9, 2005.
Co-pending U.S. Appl. No. 11/082,716, filed Mar. 16, 2005
Co-pending U.S. Appl. No. 11/303,607, filed Dec. 16, 2005.
Co-pending U.S. Appl. No. 11/404,126, filed Apr. 13, 2006.
Co-pending U.S. Appl. No. 11/584,079, filed Oct. 20, 2006.
Co-pending U.S. Appl. No. 11/586,968, filed Oct. 25, 2006.
Co-pending U.S. Appl. No. 11/590,427, filed Oct. 30, 2006.
Co-pending U.S. Appl. No. 11/592,477, filed Nov. 2, 2006.
Co-pending U.S. Appl. No. 11/606,617, filed Nov. 29, 2006.
Co-pending U.S. Appl. No. 11/633,687, filed Dec. 4, 2006.
Co-pending U.S. Appl. No. 11/634,673, filed Dec. 5, 2006.
Co-pending U.S. Appl. No. 11/634,531, filed Dec. 6, 2006.
Co-pending U.S. Appl. No. 11/654,409, filed Jan. 17, 2007.
Co-pending U.S. Appl. No. 11/710,106, filed Feb. 22, 2007.
Co-pending U.S. Appl. No. 11/715,057, filed Mar. 6, 2007.
Co-pending U.S. Appl. No. 12/101,336, filed Apr. 11, 2008.

Co-pending U.S. Appl. No. 12/101,346, filed Apr. 11, 2008.
Co-pending U.S. Appl. No. 12/140,356, filed Jun. 17, 2008.
Co-pending U.S. Appl. No. 12/204,129, filed Sep. 4, 2008.
U.S. Appl. No. 60/668,022, filed Apr. 4, 2005.
U.S. Appl. No. 60/708,206, filed Aug. 15, 2005.
U.S. Appl. No. 60/902,738, filed Feb. 21, 2007.
U.S. Appl. No. 60/955,854, filed Aug. 14, 2007.
U.S. Appl. No. 12/352,513, filed Jan. 12, 2009.
PCT Search Report for PCT/US2004/29809, dated Feb. 24, 2005.
International Search Report for Application No. PCT/US2004/029812, dated Jun. 14, 2005.
European Search Report for Application No. 05445078 dated Jun. 27, 2006.
Search Report for EP 05020602, dated Jul. 6, 2006.
PCT Search Report for PCT/U52005/046700, dated Jul. 6, 2006.
International Search Report for Application No. PCT/US2006/012487, dated Sep. 12, 2006.
International Search Report for Application No. PCT/US2006/004594, dated Nov. 3, 2006.
Search report for EP 06126082, dated May 11, 2007.
Supplementary Partial European Search Report for Application No. EP04783867 dated Jan. 29, 2008.
International Search Report for Application No. PCT/US2007/016509, dated Feb. 8, 2008.
International Search Report for EP 06123557, dated Feb. 29, 2008.
International Search Report for Application No. PCT/US2008/075191, dated Nov. 17, 2008.
Donald Voet & Judith Voet, "Molecular Physiology", Biochemistry, p. 1087-1096, vol. 64, 1990, John Wiley & Sons.
IMA-EU, Kaolin, Oct. 2006, p. 1-2.
The Merck Index; 1989, pp. 1596-1597, abstract 10021.
Le Van Mao, Raymond et al. "Mesporous Aluminosilicates prepared from Zeolites by Treatment with Ammonium Fluorosilicate." J. Mater. Chem. 1993. pp. 679-683, vol. 3, No. 6.
Dyer, A. et al. "Diffusion in heteroionic zeolites: Part 1. Diffusion of water in heteroionics natrolites." Microporous and Mesoporous Materials. 1998, pp. 27-38, vol. 21.
Wright, J.K. et al., "Thermal Injury Resulting from Application of a Granular Mineral Hemostatic Agent." The Journal of Trauma Injury, Infection, and Critical Care. 2004, pp. 224-230, vol. 57, No. 2.
Top, Ayben et al. "Silver, zinc, and copper exchange in a Na-clinoptilolite and resulting effect on antibacterial activity." Applied Clay Science. 2004, pp. 13-19, vol. 27.

* cited by examiner

CALCIUM ZEOLITE HEMOSTATIC AGENT

CROSS REFERENCE TO RELATED APPLICATION

This application claims the benefit of U.S. Provisional Patent Application Ser. No. 60/502,598 filed Sep. 12, 2003, entitled "Blood Clotting Compositions and Wound Dressings," to Francis X. Hursey, the contents of which are incorporated herein by reference.

TECHNICAL FIELD

The present invention relates to blood clotting devices (also referred to as hemostatic agents) and methods of controlling bleeding and, more particularly, to blood clotting materials and compositions and wound dressings for use as bleeding control devices.

BACKGROUND OF THE INVENTION

Blood is a liquid tissue that includes red cells, white cells, corpuscles, and platelets dispersed in a liquid phase. The liquid phase is plasma, which includes acids, lipids, solublized electrolytes, and proteins. The proteins are suspended in the liquid phase and can be separated out of the liquid phase by any of a variety of methods such as filtration, centrifugation, electrophoresis, and immunochemical techniques. One particular protein suspended in the liquid phase is fibrinogen. When bleeding occurs, the fibrinogen reacts with water and thrombin (an enzyme) to form fibrin, which is insoluble in blood and polymerizes to form clots.

In a wide variety of circumstances, animals, including humans, can be wounded. Often bleeding is associated with such wounds. In some instances, the wound and the bleeding are minor, and normal blood clotting functions in addition to the application of simple first aid are all that is required. Unfortunately, however, in other circumstances, substantial bleeding can occur. These situations usually require specialized equipment and materials as well as personnel trained to administer appropriate aid. If such aid is not readily available, excessive blood loss can occur. When bleeding is severe, sometimes the immediate availability of equipment and trained personnel is still insufficient to stanch the flow of blood in a timely manner.

Moreover, severe wounds can often be inflicted in very remote areas or in situations, such as on a battlefield, where adequate medical assistance is not immediately available. In these instances, it is important to stop bleeding, even in less severe wounds, long enough to allow the injured person or animal to receive medical attention.

In an effort to address the above-described problems, materials have been developed for controlling excessive bleeding in situations where conventional aid is unavailable or less than optimally effective. Although these materials have been shown to be somewhat successful, they are not effective enough for traumatic wounds and tend to be expensive. Furthermore, these materials are sometimes ineffective in all situations and can be difficult to apply as well as remove from a wound. Additionally, or alternatively, they can produce undesirable side effects.

Based on the foregoing, it is a general object of the present invention to provide a bleeding control device that overcomes or improves upon the prior art.

SUMMARY OF THE INVENTION

According to one aspect of the present invention, a composition for promoting the formation of clots in blood includes a binder and a zeolite disposed in the binder. The zeolite has an adjusted calcium content. A calcium content of the zeolite may be about 75 weight percent (wt. %) to about 83 wt. %. In another aspect of the present invention, a method of forming a blood-clotting composition includes the steps of providing a combination of a zeolite and a binder and adjusting a calcium content of the zeolite/binder combination with a calcium-containing compound such that upon application of the composition to a wound, a heat of hydration is reduced and thereby the heat transferred to tissue surrounding the wound is reduced. In yet a third aspect of the present invention, a method of clotting blood flowing from a wound includes applying a zeolite to the wound where bleeding is present and maintaining the zeolite in contact with the wound for a predetermined amount of time. Preferably, the zeolite has an adjusted calcium content and causes controllable blood clotting, thereby stopping or minimizing the flow of blood.

One advantage of the present invention is that it is easily applied to an open wound. Particularly when the composition is in paste, gel, or powder form, it can be readily removed from sterilized packaging and deposited directly at the points from which blood emanates to dress the wound. Alternately, the composition can be incorporated into a bandaging system and applied in conjunction with the bandaging system. By incorporating the composition into the bandaging system, the wound is treated and covered in a single step, thereby reducing the number of individual procedures required.

Another advantage of the present invention is that it rapidly and effectively promotes the clotting rate of blood. By causing blood to clot rapidly, a flow of blood can be reduced or stopped quickly.

Still another advantage is that the exothermic effects generally experienced upon application of a zeolite to blood are reduced. Because of the adjusted calcium content, a less-drastic temperature increase is realized when the zeolite contacts the blood emanating from a wound. Consequently, the discomfort experienced by a person or animal at the wound site will be minimized.

DETAILED DESCRIPTION OF THE PREFERRED EMBODIMENTS

Disclosed herein are compositions and methods directed to the clotting of blood and the dressing of wounds. The compositions generally include molecular sieves in which a calcium content is adjusted. While the structures of the molecular sieves themselves serve to minimize or stop bleeding by absorbing at least portions of the liquid phases of blood, thereby promoting clotting, the calcium components thereof facilitate the dissipation of heats of hydration upon application of the sieves to the blood. The methods generally include the application of molecular sieves to bleeding wounds to provide dressings and removing components of the blood to facilitate the formation of clots while minimizing the heats of hydration generated.

In one embodiment of the present invention, a molecular sieve comprises a zeolite having an adjusted calcium content disposed in a binder. As used herein, the term "zeolite" refers to a crystalline form of aluminosilicate that may include several ionic species including sodium and calcium moieties. The preferred molecular structure of the zeolite is referred to as an "A-type" crystal. As used herein, the term "A-type crystal" is intended to indicate a crystal having a cubic structure and round holes. Suitable zeolites for use in the applications disclosed herein are also preferably nanoporous so as to provide increased surface areas. As used herein, the term "nanoporous" is intended to indicate an average pore diameter of about 3 angstroms to about 5 angstroms.

In another embodiment of the present invention, the zeolite comprises irregularly-shaped granular material that is prepared by grinding larger particles and then selecting material that will pass through a 16 mesh sieve screen but will not pass through a 40 mesh sieve screen. The resulting zeolite is a composition of irregular granules that range in size from 0.4 millimeters (mm) in diameter to 0.8 mm in diameter.

Zeolites for use in the disclosed applications may be naturally occurring or synthetically produced. Numerous varieties of naturally occurring zeolites are found as deposits in sedimentary environments as well as in other places and typically have about 90% calcium and about 10% sodium based on the total amount of calcium and sodium ions. Naturally occurring zeolites that may be applicable to the compositions and methods described herein include, but are not limited to, analcite, chabazite, heulandite, natrolite, stilbite, and thomosonite. Synthetically produced zeolites that may also find use in the compositions and methods described herein are generally produced by processes in which rare earth oxides are substituted by silicates, alumina, or alumina in combination with alkali or alkaline earth metal oxides.

The binder is preferably clay-based and may further include fillers (e.g., aluminum sulfate) or thickening agents that facilitate the selective application of the zeolite in various forms (e.g., as a paste, gel, powder, or erodable solid member). Natural clays that may provide suitable bases include, but are not limited to, kaolin, kaolinite, bentonite, montmorillonite, combinations of the foregoing clays, and the like. Modified clays such as polyorganosilicate graft polymers may also provide suitable bases.

The zeolite used for a blood clotting composition of the present invention includes an adjusted calcium content such that the calcium content is up to about 83 wt. % calcium and preferably about 75 wt. % to about 83 wt. % calcium. Adjustment of the calcium content of the zeolite provides a controlling factor in the efficacy of the blood clotting composition of the present invention. Increasing the calcium content to such a level substantially improves and enhances blood coagulation upon application of the blood clotting composition to blood. Furthermore, the exothermic effects that result from the application of the calcium zeolite to the blood are reduced.

To prepare the calcium zeolite for the present invention, the starting zeolite may be supplemented with a calcium-containing compound. Calcium-containing compounds that may be used to supplement the zeolite include, but are not limited to, calcium oxides, calcium sulfates, calcium chlorides, and the like, as well as combinations of any of the foregoing compounds.

Because of the presence of the calcium in the zeolite material in the amount as indicated above, the zeolite material generates less heat upon being fully saturated with water in the application of the zeolite to blood. In particular, heat generated by the application of the zeolite having up to about 83 wt. % calcium is inversely proportional to the total amount of calcium in the zeolite. A zeolite having about 80 wt. % calcium will generate less heat (when applied to blood) than the same zeolite not having supplemental calcium. Thus, when applied to a bleeding wound under conditions of actual use, the exothermic effects and heat transferred to the wound are reduced.

Upon treating wounds with the present invention, the remaining blood, which includes cells, corpuscles, platelets, and plasma, is concentrated. The platelets aggregate and interact with collagen, phospholipids, and lipid-containing proteins in the plasma. The aggregation of the platelets provide nuclei upon which fibrin binds to form a clot. Cells from the blood subsequently combine with the clot to form a mass. When blood emanates from a wound, the formation of the mass from the clot causes the flow of blood to cease, thereby eliminating further loss of blood. The blood pressure will often noticeably increase upon the application of the present invention due to cessation of blood loss.

Although this invention has been shown and described with respect to the detailed embodiments thereof, it will be understood by those of skill in the art that various changes may be made and equivalents may be substituted for elements thereof without departing from the scope of the invention. In addition, modifications may be made to adapt a particular situation or material to the teachings of the invention without departing from the essential scope thereof. Therefore, it is intended that the invention not be limited to the particular embodiments disclosed in the above detailed description, but that the invention will include all embodiments falling within the scope of the appended claims.

What is claimed is:

1. A composition for promoting the formation of clots in blood, said composition comprising: a binder; a zeolite disposed in said binder, said zeolite having an adjusted calcium content via the addition of a calcium-containing compound to said zeolite, said calcium content being between about 75 wt. % to about 83 wt. %, said composition being operable to reduce a heat of hydration when exposed to blood.

2. The composition of claim 1, wherein said zeolite comprises aluminosilicate.

3. The composition of claim 1, wherein said adjusted calcium content is obtained via the addition of a calcium-containing compound to a starting zeolite, said calcium-containing compound being selected from the group consisting of calcium oxides, calcium sulfates, and calcium chlorides.

4. The composition of claim 1, wherein said zeolite is nanoporous.

5. The composition of claim 1, wherein said binder is clay-based.

6. The composition of claim 1, wherein said composition is of an irregularly-shaped granular form having a size distribution determined by sieving ground material with 40 mesh and 16 mesh cut-off screens.

7. A method of forming a blood-cloning composition, said method comprising the steps of: providing a zeolite; combining said zeolite with a binder; and adjusting a calcium content of said zeolite via the addition of a calcium-containing compound to said zeolite, said calcium content being about 75 wt. % to about 83 wt. % and such that upon application of said composition to a wound, a heat of hydration is reduced and thereby heat transferred to said wound is reduced.

8. The method of claim 7, wherein said adjusting said calcium content of said zeolite comprises supplementing said zeolite with a calcium-containing compound such that said calcium content is about 83 wt. %.

9. A method of clotting blood flowing from a wound, said method comprising the steps of:
   providing a zeolite having a calcium content adjusted via the addition of a calcium-containing compound to said zeolite, said calcium content being about 75 wt. % to about 83 wt. %, and said zeolite being disposed in a clay binder;
   applying said zeolite to said wound, said zeolite being capable of producing a controllable blood clotting effect on said wound such that a heat of hydration is reduced; and
   maintaining said zeolite in contact with said wound for an amount of time sufficient to cause blood flowing from said wound to clot.

* * * * *